US00PP15565P2

(12) United States Plant Patent
Arimitsu

(10) Patent No.: US PP15,565 P2
(45) Date of Patent: Feb. 15, 2005

(54) ***PORTULACA* PLANT NAMED 'BODHIGROS'**

(50) Latin Name: *Portulaca grandiflora*
Varietal Denomination: Bodhigros

(75) Inventor: Yoshiro Arimitsu, Lompoc, CA (US)

(73) Assignee: John Bodger & Sons Co., South El Monte, CA (US)

( * ) Notice: Subject to any disclaimer, the term of this patent is extended or adjusted under 35 U.S.C. 154(b) by 0 days.

(21) Appl. No.: 10/822,979

(22) Filed: Apr. 13, 2004

(51) Int. Cl.[7] ..... A01H 5/00
(52) U.S. Cl. ..... Plt./263
(58) Field of Search ..... Plt./263

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Portulaca* plant named 'Bodhigros', characterized by its upright, low spreading and mounded plant habit; freely branching habit; dense and bushy growth habit; continuous flowering habit; and numerous large purple-colored flowers.

1 Drawing Sheet

Botanical classification: *Portulaca grandiflora* cultivar Bodhigros.

BACKGROUND OF THE INVENTION

The present Invention relates to a new and distinct cultivar of *Portulaca* plant, botanically known as *Portulaca grandiflora,* and hereinafter referred to by the cultivar name Bodhigros.

The new *Portulaca* is a product of a planned breeding program conducted by the Inventor in Lompoc, Calif. The objective of the breeding program is to create new *Portulacas* with dense plant habit, numerous large flowers and attractive flower coloration.

The new *Portulaca* originated from a self-pollination made by the Inventor of a proprietary *Portulaca* seedling selection identified as code number 2PR65-2, not patented. The new *Portulaca* was selected as a single plant from the resulting progeny of the self-pollination by the Inventor in a controlled environment in Lompoc, Calif.

Asexual reproduction of the new cultivar by vegetative cuttings in Lompoc, Calif. since May, 2000 has shown that the unique features of this new *Portulaca* are stable and reproduced true to type in successive generations.

SUMMARY OF THE INVENTION

Plants of the cultivar Bodhigros have not been observed under all possible environmental conditions. The phenotype may vary somewhat with variations in environment such as temperature and light intensity without, however, any variance in genotype.

The following traits have been repeatedly observed and are determined to be the unique characteristics of 'Bodhigros'. These characteristics in combination distinguish 'Bodhigros' as a new and distinct cultivar:

1. Upright, low spreading and mounded plant habit.
2. Freely branching habit; dense and bushy growth habit.
3. Continuous flowering habit.
4. Numerous large purple-colored flowers.

Compared to plants of the parent selection, plants of the new *Portulaca* differ in flower color, have a denser growth habit and flower continuously.

Plants of the new *Portulaca* can be compared to plants of the seed-propagated cultivar Sundial Pink, not patented. In side-by-side comparisons conducted in Lompoc, Calif., plants of the new *Portulaca* differed from plants of the cultivar Sundial Pink in the following characteristics:

1. Plants of the new *Portulaca* had a denser growth habit than plants of the cultivar Sundial Pink.
2. Plants of the new *Portulaca* flowered continuously whereas plants of the cultivar Sundial Pink flowered intermittently.
3. Flowers of plants of the new *Portulaca* did not produce pollen whereas flowers of plants of the cultivar Sundial Pink produced pollen.

Plants of the new *Portulaca* can be compared to plants of the seed-propagated cultivar Margarita Rosita, not patented. In side-by-side comparisons conducted in Lompoc, Calif., plants of the new *Portulaca* differed from plants of the cultivar Margarita Rosita in the following characteristics:

1. Plants of the new *Portulaca* were more vigorous than plants of the cultivar Margarita Rosita.
2. Plants of the new *Portulaca* had larger flowers than plants of the cultivar Margarita Rosita.
3. Flowers of plants of the new *Portulaca* did not produce pollen whereas flowers of plants of the cultivar Margarita Rosita produced pollen.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Portulaca.*

The photograph at the bottom of the sheet comprises a side perspective view of a typical flowering plant of 'Bodhigros' grown in a container.

The photograph at the top of the sheet comprises a close-up view of typical flowers of 'Bodhigros'.

DETAILED BOTANICAL DESCRIPTION

The aforementioned photographs and following observations and measurements describe plants grown in Lompoc, Calif., under commercial practice during the winter in a polycarbonate-covered greenhouse with day temperatures about 21 to 24° C., night temperatures about 16 to 18° C. and light levels about 5,000 to 9,000 foot-candles. Plants were grown with one rooted cutting per 15.25-cm container for about eleven weeks. In the following description, color references are made to The Royal Horticultural Society Colour Chart, 1995 Edition, except where general terms of ordinary dictionary significance are used.

Botanical classification: *Portulaca grandiflora* cultivar Bodhigros.

Parentage:

*Female parent.*—Proprietary *Portulaca* seedling selection identified as 2PR65-2, not patented.

*Male parent.*—Proprietary *Portulaca* seedling selection identified as 2PR65-2, not patented.

Propagation:

*Type cutting.*—Vegetative cuttings.

*Time to initiate roots.*—About 7 to 10 days at 24° C.

*Time to develop roots.*—About two to three weeks at 24° C.

*Root description.*—Fine, fibrous, whitish in color.

*Rooting habit.*—Freely branching.

Plant description:

*Form.*—Annual flowering plant; upright, low spreading and mounded plant habit. Moderately vigorous. Freely branching with about six primarily lateral branches and numerous secondary laterals per plant; dense and bushy growth habit.

*Plant height.*—About 12 cm.

*Plant diameter.*—About 20 cm.

*Lateral branches.*—Length: About 15 cm. Diameter: About 3 mm. Internode length: About 8 mm. Texture: Pubescence at nodes; succulent. Color: 146B.

*Foliage description.*—Arrangement: Alternate, simple. Length: About 1.5 cm. Width: About 2.5 mm. Shape: Lanceolate. Apex: Acute. Base: Attenuate. Margin: Entire. Texture, upper and lower surfaces: Smooth, glabrous; succulent. Venation pattern: Parallel. Color: Developing foliage, upper and lower surfaces: 144A. Fully expanded foliage, upper and lower surfaces: 146A. Venation, upper and lower surfaces: 146A. Petiole length: About 1 mm. Petiole diameter: About 1 mm. Petiole color: 144B.

Flower description:

*Flower type and habit.*—Large radial cup-shaped flowers; flowers face upward or outward; single, axillary. Flowers persistent. Freely flowering, typically nine to eleven open flowers and flower buds per plant at one time.

*Natural flowering season.*—Spring until frost in the autumn; flowering continuous during the flowering period.

*Flower longevity on the plant.*—About seven to ten days.

*Fragrance.*—None detected.

*Flower diameter.*—About 4 cm.

*Flower depth (height).*—About 2 cm.

*Flower buds.*—Length: About 1.1 cm. Diameter: About 6 mm. Shape: Ovoid. Color: 78B.

*Petals.*—Arrangement/appearance: About 24 petals arranged in about three whorls; imbricate. Length: About 2 cm. Width: About 1.6 cm. Shape: Cordate. Apex: Emarginate. Base: Attenuate. Margin: Entire. Texture, upper and lower surfaces: Smooth, satiny. Color: When opening, upper surface: 78A. When opening, lower surface: 78B. Fully opened, upper surface: 78B; towards the base, 157B. Fully opened, lower surface: 78B to 78C.

*Sepals.*—Arrangement/appearance: Two sepals, opposite. Length: About 7 mm. Width: About 6 mm. Shape: Elliptic. Apex: Acute. Base: Truncate. Margin: Entire. Texture, upper and lower surfaces: Smooth, glabrous. Color, upper and lower surfaces: 146B to 146C.

*Peduncles.*—Length: About 1 mm. Width: About 1 mm. Strength: Strong. Texture: Smooth, glabrous. Color: 146B.

*Reproductive organs.*—Stamens: Quantity per flower/arrangement: About 30 fused in a ring surrounding the ovary. Anther shape: Elongated oval. Anther length: Less than 1 mm. Anther color: 23A. Pollen amount: None observed. Pistils: Quantity per flower: One. Pistil length: About 1.2 cm. Stigma shape: Eight-parted. Stigma color: 37C. Style length: About 5 mm. Style color: 73A. Ovary color: 152D.

*Fruit/seed.*—Fruit and seed production has not been observed.

Disease/pest resistance: Plants of the new *Portulaca* have not been noted to be resistant to pathogens and pests common to *Portulaca*.

It is claimed:

1. A new and distinct cultivar of *Portulaca* plant named 'Bodhigros', as illustrated and described.

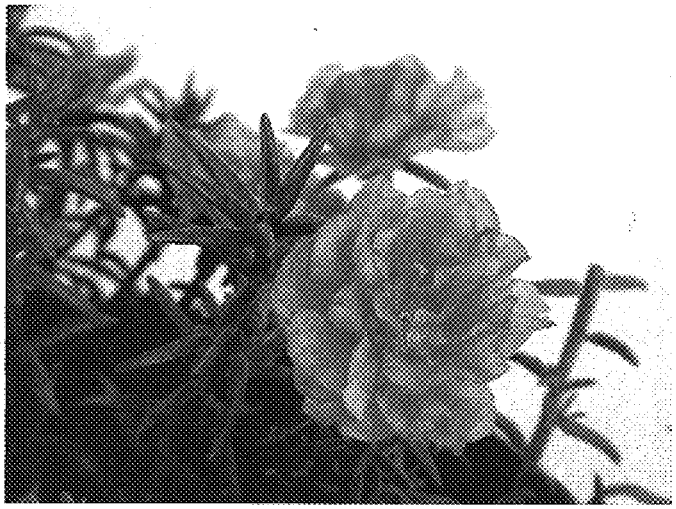
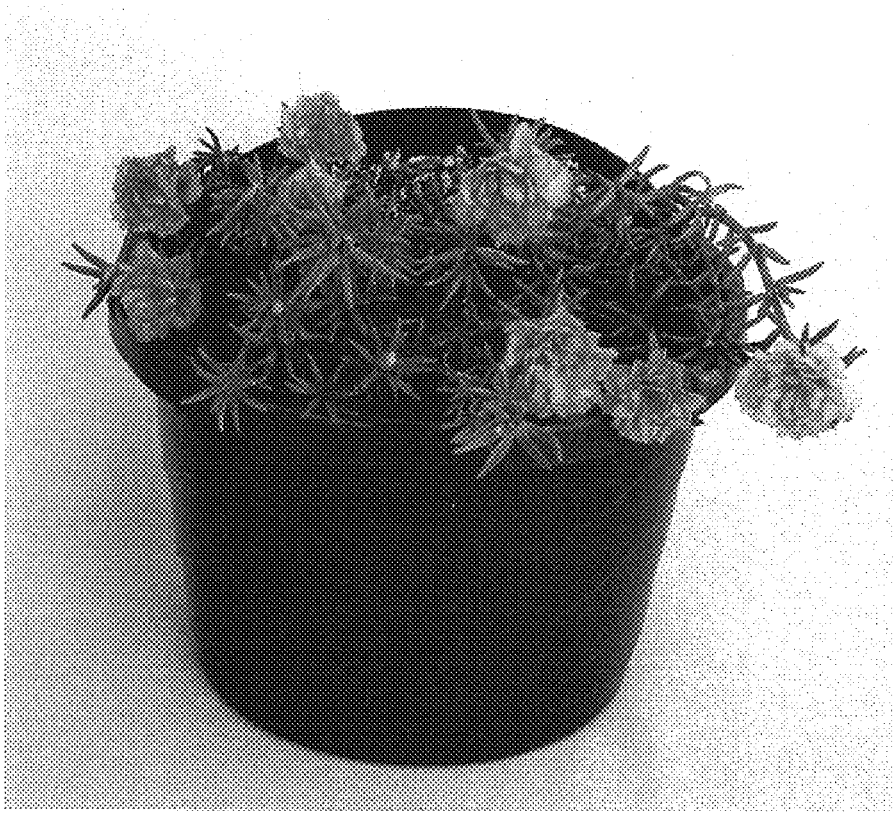

* * * * *